United States Patent
Chen et al.

(10) Patent No.: US 10,034,779 B2
(45) Date of Patent: Jul. 31, 2018

(54) METHOD AND SYSTEM FOR ACQUIRING ATTITUDE OF ACETABULUM AND FEMORAL HEAD IN REAL TIME DURING HIP JOINT REPLACEMENT PROCEDURE

(71) Applicant: Hong Chen, Beijing (CN)

(72) Inventors: Hong Chen, Beijing (CN); Zhihua Wang, Beijing (CN); Yixin Zhou, Beijing (CN); Shaojie Su, Beijing (CN); Tianjia Sun, Beijing (CN); Jiyang Gao, Beijing (CN); Hanjun Jiang, Beijing (CN)

( * ) Notice: Subject to any disclaimer, the term of this patent is extended or adjusted under 35 U.S.C. 154(b) by 818 days.

(21) Appl. No.: 14/440,594

(22) PCT Filed: Oct. 8, 2012

(86) PCT No.: PCT/CN2012/082537
§ 371 (c)(1),
(2) Date: May 4, 2015

(87) PCT Pub. No.: WO2013/170573
PCT Pub. Date: Nov. 21, 2013

(65) Prior Publication Data
US 2015/0289890 A1    Oct. 15, 2015

(30) Foreign Application Priority Data
May 14, 2012  (CN) .......................... 2012 1 0148587

(51) Int. Cl.
*A61F 2/46*  (2006.01)
*A61F 2/36*  (2006.01)
*A61F 2/30*  (2006.01)

(52) U.S. Cl.
CPC .......... *A61F 2/4684* (2013.01); *A61F 2/4657* (2013.01); *A61F 2/3609* (2013.01);
(Continued)

(58) Field of Classification Search
CPC ........ A61F 2/36; A61F 2/3601; A61F 2/3609; A61F 2/4657; A61F 2/4684;
(Continued)

(56) References Cited

U.S. PATENT DOCUMENTS

| 6,447,448 B1 * | 9/2002 | Ishikawa .............. A61B 5/0031 128/899 |
| 7,458,989 B2 * | 12/2008 | Banks .................. A61B 5/6846 600/300 |

(Continued)

*Primary Examiner* — Eric S Gibson
(74) *Attorney, Agent, or Firm* — Novoclaims Patent Services LLC; Mei Lin Wong

(57) ABSTRACT

A method and system for acquiring the attitudes of an acetabulum and a femoral head in real time during an artificial hip joint replacement procedure; during hip joint replacement, a pressure sensor and/or a touch sensor are disposed at each pressure point concerned for a femoral head prosthesis test mold, forming a sensor array (1); the sensor array (1) acquires the contact and stress conditions between the femoral head prosthesis test mold and the acetabulum, and sends out a signal; and a receiving terminal receives and displays the signal on a display module, and acquires the simulated attitudes of the acetabulum and the femoral head. The system comprises a sensor array (1), a necessary peripheral circuit, and a signal receiving and display device for receiving and displaying the signal sent by the peripheral circuit. The present invention can accurately simulate the presented attitude of the femoral head prosthesis during hip joint replacement procedure, so that a doctor can intuitively see the position and movement condition of the femoral head prosthesis during the procedure, thus improving the success rate and curative effect of the hip joint replacement procedure.

5 Claims, 2 Drawing Sheets

(52) U.S. Cl.
CPC .............. *A61F 2002/30668* (2013.01); *A61F 2002/4666* (2013.01); *A61F 2002/4668* (2013.01)

(58) Field of Classification Search
CPC ...... A61F 2002/3611; A61F 2002/3613; A61F 2002/3615; A61F 2002/3617; A61F 2002/3619; A61F 2002/3621; A61F 2002/365; A61F 2002/4666; A61F 2002/4668
See application file for complete search history.

(56) References Cited

U.S. PATENT DOCUMENTS

| | | | | |
|---|---|---|---|---|
| 8,661,893 | B2* | 3/2014 | Stein | A61B 5/686 600/587 |
| 8,956,418 | B2* | 2/2015 | Wasielewski | A61B 5/03 600/309 |
| 9,216,086 | B2* | 12/2015 | Conrad | A61F 2/4684 |
| 9,308,102 | B2* | 4/2016 | McCarthy | A61F 2/4684 |
| 2004/0243148 | A1* | 12/2004 | Wasielewski | A61B 17/00 606/130 |
| 2005/0012610 | A1* | 1/2005 | Liao | A61B 5/0008 340/539.12 |
| 2005/0027192 | A1* | 2/2005 | Govari | A61B 5/06 600/424 |
| 2006/0095047 | A1* | 5/2006 | de la Barrera | A61F 2/4657 606/102 |
| 2006/0271199 | A1* | 11/2006 | Johnson | A61B 5/06 623/18.12 |
| 2007/0005145 | A1* | 1/2007 | Banks | A61B 5/6846 623/23.42 |
| 2007/0088442 | A1* | 4/2007 | Cima | A61B 5/055 623/18.11 |
| 2007/0234819 | A1* | 10/2007 | Amirouche | A61F 2/389 73/781 |
| 2008/0065225 | A1* | 3/2008 | Wasielewski | A61B 5/03 623/18.11 |
| 2010/0076505 | A1* | 3/2010 | Borja | A61F 2/4657 606/86 R |
| 2010/0100011 | A1* | 4/2010 | Roche | A61B 5/103 600/587 |
| 2010/0249777 | A1* | 9/2010 | Sherman | A61B 5/1107 606/53 |
| 2011/0264009 | A1* | 10/2011 | Walter | A61B 5/4504 600/595 |
| 2011/0319755 | A1* | 12/2011 | Stein | A61B 5/0031 600/437 |
| 2012/0216611 | A1* | 8/2012 | Stein | A61B 5/686 73/379.01 |
| 2013/0197656 | A1* | 8/2013 | Conrad | A61F 2/4684 623/22.11 |
| 2013/0253378 | A1* | 9/2013 | Claypool | A61F 2/389 600/595 |
| 2013/0261502 | A1* | 10/2013 | Sherman | A61F 2/4657 600/587 |
| 2014/0249535 | A1* | 9/2014 | McCarthy | A61F 2/4684 606/91 |
| 2015/0105782 | A1* | 4/2015 | D'Lima | A61B 17/025 606/90 |
| 2015/0282888 | A1* | 10/2015 | Olson | A61B 1/0661 600/249 |
| 2015/0289890 | A1* | 10/2015 | Chen | A61F 2/4657 606/102 |
| 2015/0297362 | A1* | 10/2015 | Singh | A61F 2/4657 623/22.15 |
| 2016/0175116 | A1* | 6/2016 | Bader | A61F 2/4657 606/86 R |
| 2016/0278944 | A1* | 9/2016 | D'Lima | A61F 2/4657 |

* cited by examiner

METHOD AND SYSTEM FOR ACQUIRING ATTITUDE OF ACETABULUM AND FEMORAL HEAD IN REAL TIME DURING HIP JOINT REPLACEMENT PROCEDURE

CROSS-REFERENCE TO RELATED APPLICATIONS

This application is a National Stage Appl. filed under 35 USC 371 of International Patent Application No. PCT/CN2012/082537 with an international filing date of Oct. 8, 2012, designating the United States, and further claims priority benefits to Chinese Patent Application No. 201210148587.1 filed May 14, 2012.

FIELD OF THE INVENTION

The invention relates to the field of medical electronic technology, and more particularly to a method and a system for acquiring relative pose between an acetabulum and a femoral head in hip replacement in real time.

BACKGROUND OF THE INVENTION

Artificial joint replacement has been gradually developed since 1960s, and numerous patients with joint disease benefit from the hip replacement. The hip replacement, as an example, is widely applied for treatment of osteoarthritis, aseptic bone necrosis (such as femoral head necrosis), hip fracture (such as femoral neck fracture), rheumatoid arthritis, traumatic arthritis, benign and malignant bone tumor, and ankylosing spondylitis. The hip replacement is widely applied in the above joint diseases. With the increasing aging population, the number of patients with osteoarthritis presents a rising trend, so that more and more artificial joint replacement surgeries are conducted each year.

However, there is a need for improvement of the hip replacement in some aspects. In current hip replacement, the process of mounting the femoral head prosthesis into the acetabulum is operated by the doctor totally based on the practice experience thereof. The doctor cannot directly observe the motion of the femoral head prosthesis in the acetabulum so that whether the femoral head trial is mounted in the appropriate position of the acetabulum cannot be specifically ensured. If the mounting position of the prosthesis is inaccurate in the hip replacement, motion limitation or dislocation may occur in post-operation, or the reduction of the service life will occur as the force exerted on the prosthesis is uneven and the abrasion is accelerated over a long period. In general, a success hip replacement surgery is adapted to provide a service time at least 20 years. However, a positioning deviation resulting in uneven force exerted on the joint would decrease the service life of the artificial hip to between 7 and 8 years or even shorter.

SUMMARY OF THE INVENTION

In view of the above-described problems, it is one objective of the invention to provide a method and a system for acquiring and simulating the relative pose between an acetabulum and a femoral head in hip replacement in real time. The method and the system are adapted to exactly simulate the relative position of the femoral head prosthesis in the acetabulum and enable the doctors to directly observe the position and the motion of the prosthesis during the operation, thereby greatly improving the success rate of the hip replacement and the surgery effect.

To achieve the above objective, technical scheme of the invention is as follows:

A method for real-time acquiring relative pose between an acetabulum and a femoral head in hip replacement comprises: disposing pressure sensors and/or touch sensors at concerned pressure positions on a femoral head trial whereby forming a sensor array; acquiring signals of interactive contacts and forces between the femoral head trial and the acetabulum by the sensor array, and transmitting the signals wirelessly; and receiving the signals by a wireless receiver and displaying the signals by a display module whereby simulating relative pose between the acetabulum and the femoral head in real time.

In addition, the method further comprises disposing an image sensor inside the femoral head trial to acquire position information of the femoral head trial which is then transmitted to the display module. Acquisition of the position information of the femoral head trial is realized by printing previously-designed patterns on the inner side of the acetabulum and taking images of them by the image sensor.

A system for the method of acquiring relative pose in real time between an acetabulum and a femoral head in hip replacement is also provided. The system comprises: the sensor array, the sensor array comprising a plurality of the pressure sensors and/or the touch sensors, the pressure sensors and/or the touch sensors being disposed on the concerned pressure points in the hip replacement on the femoral head trial; a peripheral circuit for processing and transmitting the signals acquired by the sensor array; and a signal receiving and displaying device for receiving and displaying signals transmitted from the peripheral circuit.

Preferably, the sensor array further comprises an image sensor disposed inside the femoral head trial.

The peripheral circuit comprises: a signal amplifier, a first microprocessor, and a first wireless transceiver. The signal amplifier is connected to the output of the sensor array to realize signal amplification and analog-digital conversion. The first microprocessor is connected to the output of the signal amplifier. The first microprocessor controls the sensor array and the signal amplifier operating normally, conducts parallel-series conversion on the digital signals of the sensors, and packs the digital signals. The first wireless transceiver is connected to the output of the first microprocessor and sends out packed data. The signal receiving and displaying device comprises: a second wireless transceiver, a second microprocessor, and a display module. The second wireless transceiver receives the data transmitted from the first wireless transceiver. The second microprocessor receives the data from the second wireless transceiver, processes the digital signals of the sensors, and changes them into a form convenient for operators to observe. The display module is connected to the second microprocessor for displaying the result of the second microprocessor.

Optionally, the output of the first microprocessor can be directly connected to the input of the second microprocessor, that is, the wireless transceivers are deleted and replaced by a wired mode to transmit data.

In addition, a permanent magnet can be added on the acetabulum together with a single-axis or multi-axis magnetometer being mounted in the femoral head trial, whereby measuring a relative angle between the acetabulum and the femoral head.

The system is powered by batteries disposed inside or an external power supply.

One end of the femoral head trial is a hemispherical shell. Holes are distributed on the hemispherical shell for mounting pressure sensors or touch sensors and ground wires.

Distribution of the mounting holes on the hemispherical shell is as follows: one of the mounting holes is disposed at the center of the top of the hemispherical shell. Others are disposed on the hemispherical shell at 5 circles surrounding the center.

Preferably, a pressure/touch sensor is mounted in the hole disposed at the top-center of the hemispherical shell. Downward from the top-center hole, a first circle is formed by eight evenly distributed mounting holes where four pressure/touch sensors and four ground points are alternately disposed. For a second circle to a fifth circle downward, each circle is provided with twelve pressure/touch sensors, and adjacent pressure/touch sensors are spaced at a center angle of 30°. Twelve ground points are alternately arranged among the pressure/touch sensors on the fourth circle.

A bottom part of the femoral head trial is a hemispherical shell connected to a hollow stem. A plurality of contact points are distributed symmetrically on the flank of the stem. An auxiliary sensor is disposed at each contact point and is connected to an alarm device through the peripheral circuit.

Such a method or system for acquiring relative pose in real time between the acetabulum and the femoral head has not yet been disclosed before the application of the invention. By adopting the method and the system according to embodiments of the invention, doctors are capable of directly observing the position and motion of the femoral head prosthesis, thereby improving the efficiency and efficacy of the surgery.

DETAILED DESCRIPTION OF THE EMBODIMENTS

For further illustrating the invention, experiments detailing a method and a system for acquiring relative pose in real time between an acetabulum and a femoral head in hip replacement are described below. It should be noted that the following examples are intended to describe and not to limit the invention.

A method for acquiring relative pose in real time between an acetabulum and a femoral head in hip replacement is provided. The method comprises: disposing pressure sensors and/or touch sensors on concerned pressure positions in the hip replacement on a femoral head trial to form a sensor array; acquiring interactive contact and force between the femoral head trial and the acetabulum by the sensor array and sending out signals; receiving the signals by a receiving terminal and displaying the signals on a display module whereby acquiring a simulated relative pose of the femoral head in the acetabulum in real time. The signals can be transmitted in a wireless form or a wired form. Doctors are capable of positioning the femoral head trial according to the simulation of the relative pose. When an appropriate position is found, the femoral head trial is substituted by proper femoral head prosthesis for conducting the hip replacement.

Optionally, pre-designed patterns are printed on the inner side of the acetabulum. Images of the patterns on the inner side of the acetabulum are acquired by an image sensor to obtain relative pose information.

Figure 1:
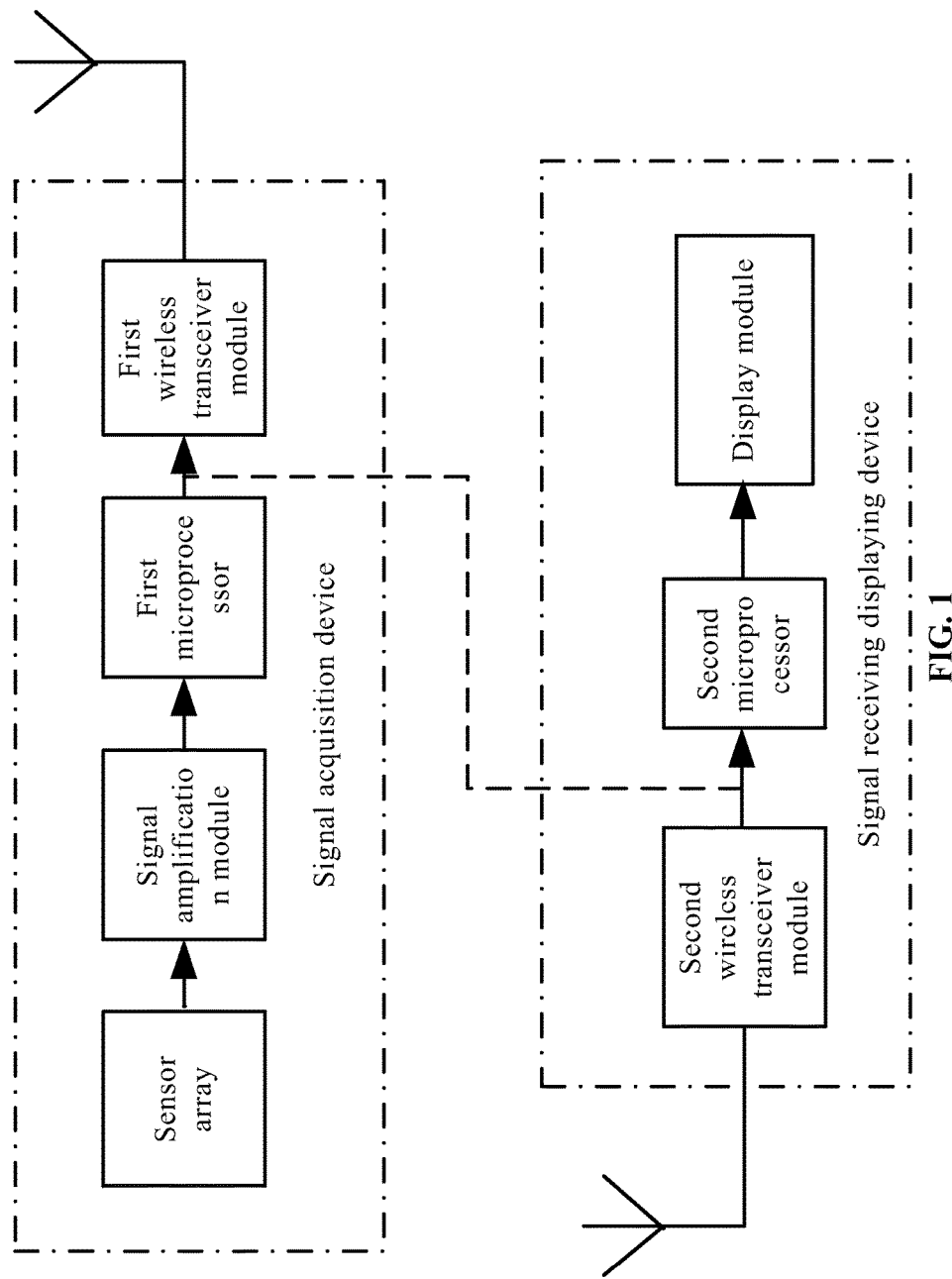
FIG. 1 is a circuit block diagram of a system for acquiring relative pose in real time between an acetabulum and a femoral head in hip replacement in accordance with one embodiment of the invention.

A system for realizing the above the method is provided. As shown in FIG. 1, the system for acquiring the relative pose between the femoral head and the acetabulum comprises: a signal acquisition device and a signal receiving displaying device. The signal acquisition device comprises: a sensor array, a signal amplifier, a first microprocessor, and a first wireless transceiver. The signal receiving displaying device comprises: a second wireless transceiver, a second microprocessor, and a display module. The first wireless transceiver transmits information of the first microprocessor in the wireless form, and the second wireless transceiver receives the information and transmits the information to the second microprocessor, thereby realizing the wireless transmission of the information. Also, the first microprocessor and the second microprocessor can be directly connected via a wire, thereby realizing information transmission in the wired form.

Figure 2:
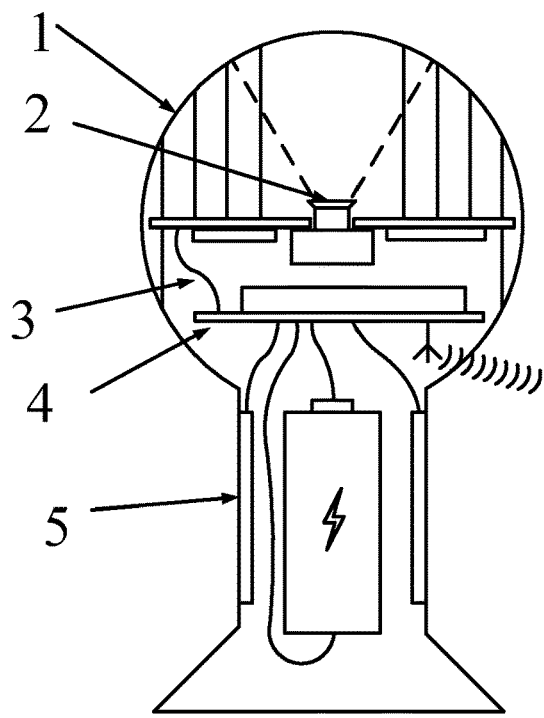
FIG. 2 is a mechanical structure diagram of a pressure acquisition device in accordance with one embodiment of the invention.

The sensor array comprises: a plurality of the pressure sensors and/or the touch sensors disposed at the concerned pressure positions on the femoral head trial, and an image sensor disposed inside the femoral head trial. The trial and the sensors can adopt a mechanical structure as shown in FIG. 2. An end of the trial is a hemispherical shell where mounting holes are distributed for disposing the pressure/touch sensors 1 and the ground wires. The pressure/touch sensors 1 are mounted in the mounting holes. The image sensor 2 is mounted in the center of the femoral head trial. After wires 3 connected to the image sensor 2 are led out, the internal part of the hemisphere is filled with a gel to solidify the internal part thereof.

An external part of the hemisphere is provided with a sealed case (in the presence of mounting holes) possessing sealing and waterproof performances.

Figure 3:
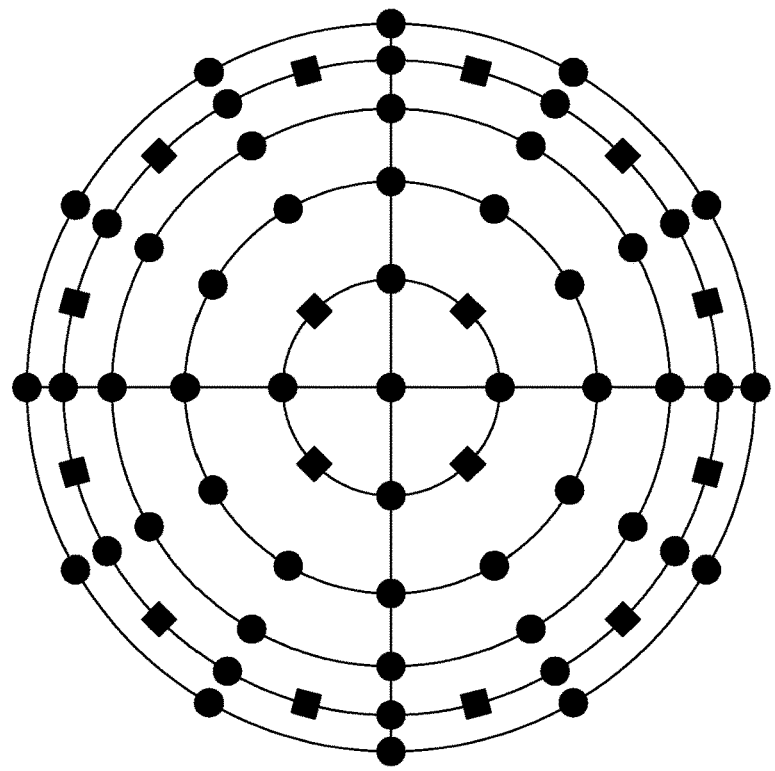
FIG. 3 is a top view showing distribution of pressure/touch sensors and ground points on a femoral head trial, in which, a circle points represents a pressure/touch sensor, and a square point represents a ground point.

The distribution of the mounting holes on the hemispherical shell is shown in FIG. 3.

One of the mounting holes is disposed at the center of the top of the hemispherical shell.

Downwards from the top, mounting holes are symmetrically arranged to form five circles. The angle between the horizontal line and each connecting line between the edge of each circle and the sphere center is 67.5°, 52.5°, 37.5°, 22.5°, and 7.5°, respectively, from top to bottom.

Rules for distribution of the sensors and the ground wires in the mounting holes are as follows:

One of the pressure/touch sensors 1 is disposed in the mounting hole at the top-center of the hemispherical shell.

Downward from the top of the hemispherical shell, a first circle is formed by eight evenly distributed mounting holes where four pressure/touch sensors 1 and four ground points are alternately disposed.

For a second circle to a fifth circle downward from the top of the hemispherical shell, each circle is provided with twelve pressure/touch sensors 1. Adjacent pressure/touch sensors 1 are spaced at a center angle of 30°. Besides, twelve ground points are alternately arranged among the pressure/touch sensors on the fourth circle. Thus, adjacent mounting holes on the fourth circle are spaced at a center angle of 15°, and a total of 52 data points and 17 ground points are distributed on the whole hemispherical shell.

Meanwhile, a bottom part of the femoral head trial is a hemispherical shell connected to a hollow stem. A circuit board 4 integrated with the signal amplifier, the first microprocessor, and the first wireless transceiver is disposed in the hollow position of the hemispherical shell. Six contact points 5 are symmetrically arranged on the flank of the stem. An auxiliary sensor is disposed at each of the contact points 5. The auxiliary sensor is connected to the first microprocessor via the signal amplifier, and the microprocessor is connected to an alarm device and initiates the alarm device according to the signal from the auxiliary sensor.

Working process of the system of the invention is as follows:

The femoral head trial is employed by a doctor for positioning. The pressure/touch sensors are mounted at the concerned pressure points in the hip replacement, and such pressure points are predictable for the doctor. Meanwhile, pre-designed patterns are printed on the inner side of the acetabulum and the image sensor is disposed in the internal part of the femoral head trial to take images of the patterns. As a result, the relative pose of the femoral head trial and the acetabulum is obtained by analyzing the force/contact information and images. The force/contact signals are amplified and A/D converted, and then input into the first microprocessor. The first microprocessor controls the sensor array and the signal amplifier operating normally, conducts parallel-series conversion on received digital signals, and packs the signals. The first wireless transceiver sends out the packed data. The data are received by the second wireless transceiver arranged at the external. Both the first and the second wireless transceivers can communicate in Bluetooth mode. The second wireless transceiver inputs the received data into the second microprocessor. The second microprocessor processes the digital pressure signals into an observable form and displays the information on the display module. A PC or a tablet PC can act as the second microprocessor and the display module in practice. Thus, the contact condition and the pressure distribution condition on each part of the trial surface are acquired by the doctor in real time, and exact position of the trial in the acetabulum is known, so that a pressure balance position is found for conducting exact positioning. After the positioning, the trial is substituted by appropriate femoral head prosthesis.

Furthermore, because the auxiliary sensors, which can also be pressure/touch sensors, are disposed on the flank side of the stem of the femoral head trial, when the auxiliary sensor contacts with the acetabulum, it indicates that the femoral head trial is about to dislocate. Signals from the auxiliary sensors are amplified by the signal amplifier and input into the first microprocessor. The first microprocessor initiates the connected alarm device according to the signals from the auxiliary sensors to give out a warning which indicates that the present prosthesis position will result in subluxation or complete dislocation.

According to the practical condition, the pressure/touch sensor and the image sensor can be adopted as the sensor types of the sensor array for the purpose of perceiving the interactive contacts and forces and the relative pose between the femoral head trial and the acetabulum, thereby determining whether or not the position of the femoral head trial is appropriate. The specific distribution of the pressure/touch sensors and the image sensor are variable according to practical conditions, such as the size of the femoral head trial.

The invention claimed is:

1. A system for real-time acquiring relative positions between an acetabulum and a femoral head in hip replacement according to a method for real-time acquiring relative positions between an acetabulum and a femoral head in hip replacement, wherein the method comprises the steps of:

disposing pressure sensors and/or touch sensors at pressure-concerning positions in the hip replacement on a femoral head template thereby forming a sensor array;

acquiring signals of interactive contacts and forces between the femoral head template and the acetabulum by the sensor array, and transmitting the signals wirelessly; and receiving the signals by a wireless receiver and displaying the signals by a display module whereby simulating relative positions between the acetabulum and the femoral head in real time, the system comprising:

the sensor array, the sensor array comprising a plurality of the pressure sensors and/or the touch sensors, the pressure sensors and/or the touch sensors being disposed on pressure points of interest in the hip replacement on the femoral head template;

an external circuit, being configured to process and transmit the signals acquired by the sensor array; and a signal receiving displaying device, being configured to receive and display signals transmitted from the external circuit;

wherein the sensor array further comprises an image sensor disposed inside the femoral head template, wherein the external circuit comprises:

a signal amplification module, being connected to an output of the sensor array and realizing amplification and digital-analog conversion of the signals from the sensors;

a first microprocessor, being connected to an output of the signal amplification module, controlling normal operation of the sensor array and the signal amplification module, conducting series/parallel processing on the digital signals of the sensors, and packing and transmitting the digital signals; and a first wireless transceiver module, being connected to an output of the first microprocessor and sending out data; and the signal receiving displaying device comprises:

a second wireless transceiver module for receiving the data transmitted from the first wireless transceiver module;

a second microprocessor for receiving the data from the second wireless transceiver module and processing the digital signals of the sensors into a form convenient for observation of an operator; and a display module, being connected to the second microprocessor for displaying a processing result of the second microprocessor.

2. A system for real-time acquiring relative positions between an acetabulum and a femoral head in hip replacement according to a method for real-time acquiring relative positions between an acetabulum and a femoral head in hip replacement, wherein the method comprises the steps of:

disposing pressure sensors and/or touch sensors at pressure-concerning positions in the hip replacement on a femoral head template thereby forming a sensor array;

acquiring signals of interactive contacts and forces between the femoral head template and the acetabulum by the sensor array, and transmitting the signals wirelessly; and receiving the signals by a wireless receiver and displaying the signals by a display module whereby simulating relative positions between the acetabulum and the femoral head in real time, the system comprising:

the sensor array, the sensor array comprising a plurality of the pressure sensors and/or the touch sensors, the pressure sensors and/or the touch sensors being disposed on pressure points of interest in the hip replacement on the femoral head template;

an external circuit, being configured to process and transmit the signals acquired by the sensor array; and a signal receiving displaying device, being configured to receive and display signals transmitted from the external circuit;

wherein the sensor array further comprises an image sensor disposed inside the femoral head template, wherein the external circuit comprises:

a signal amplification module, being connected to an output of the sensor array and realizing amplification and digital-analog conversion of the signals from the sensors; and a first microprocessor, being connected to an output of the signal amplification module, controlling normal operation of the sensor array and the signal amplification module, conducting series/parallel processing on the digital signals of the sensors, and packing and transmitting the signals; and the signal receiving displaying device comprises:

a second microprocessor for connecting to a signal output end of the first microprocessor and processing the digital signals of the sensors into a form convenient for observation of an operator; and a display module, being connected to the second microprocessor for displaying a processing result of the second microprocessor.

3. The system of claim 2, wherein one end of the femoral head template is a hemispherical surface; and mounting holes are distributed on the hemispherical surface of the femoral head template for mounting the pressure sensors or the touch sensors and ground wires, wherein distribution of the mounting holes on the hemispherical surface is as follows:

one of the mounting holes is disposed at a center of a top of the hemispherical surface;

downwards from the top, mounting holes are symmetrically arranged to form five circles; and an angle between a horizontal line and a connecting line between an edge of each circle and a sphere center is 67.5°, 52.5°, 37.5°, 22.5°, and 7.5°, respectively, from top to bottom.

4. The system of claim 2, wherein one end of the femoral head template is a hemispherical surface; and mounting holes are distributed on the hemispherical surface of the femoral head template for mounting the pressure sensors or the touch sensors and ground wires, wherein one of the pressure sensors or touch sensors is disposed in the mounting hole of the top of the hemispherical surface;

downward from the top of the hemispherical surface, a first circle is formed by eight evenly distributed mounting holes where four pressure sensors or touch sensors and four ground points are alternately disposed; and for a second circle to a fifth circle downward from the top of the hemispherical surface, each circle is provided with twelve pressure sensors or touch sensors; adjacent mounting holes receiving the pressure sensors or the touch sensors are spaced at a center angle of 300; and twelve ground points are alternately arranged among the pressure sensors or the touch sensors on a fourth circle.

5. A system for real-time acquiring relative positions between an acetabulum and a femoral head in hip replacement according to a method for real-time acquiring relative positions between an acetabulum and a femoral head in hip replacement, wherein the method comprises the steps of:

disposing pressure sensors and/or touch sensors at pressure-concerning positions in the hip replacement on a femoral head template thereby forming a sensor array;

acquiring signals of interactive contacts and forces between the femoral head template and the acetabulum by the sensor array, and transmitting the signals wirelessly; and receiving the signals by a wireless receiver and displaying the signals by a display module whereby simulating relative positions between the acetabulum and the femoral head in real time, the system comprising:

the sensor array, the sensor array comprising a plurality of the pressure sensors and/or the touch sensors, the pressure sensors and/or the touch sensors being disposed on pressure points of interest in the hip replacement on the femoral head template;

an external circuit, being configured to process and transmit the signals acquired by the sensor array; and a signal receiving displaying device, being configured to receive and display signals transmitted from the external circuit;

wherein the sensor array further comprises an image sensor disposed inside the femoral head template, wherein one end of the femoral head template is a hemispherical surface; and mounting holes are distributed on the hemispherical surface of the femoral head template for mounting the pressure sensors or the touch sensors and ground wires, wherein a bottom part of the hemispherical surface is connected to a hollow neck region;

a plurality of contact points are distributed symmetrically on one side of the neck region; and an auxiliary sensor is disposed at each contact point and is connected to an alarm device via the external circuit.

* * * * *